(12) United States Patent
Schick

(10) Patent No.: US 6,908,307 B2
(45) Date of Patent: Jun. 21, 2005

(54) DENTAL CAMERA UTILIZING MULTIPLE LENSES

(75) Inventor: David B. Schick, Flushing, NY (US)

(73) Assignee: Schick Technologies, Long Island City, NY (US)

( * ) Notice: Subject to any disclaimer, the term of this patent is extended or adjusted under 35 U.S.C. 154(b) by 67 days.

(21) Appl. No.: 10/356,572

(22) Filed: Feb. 3, 2003

(65) Prior Publication Data

US 2004/0152037 A1 Aug. 5, 2004

(51) Int. Cl.$^7$ ............................................. A61C 3/00
(52) U.S. Cl. ..................... 433/29; 600/173; 396/322; 396/323
(58) Field of Search ............................ 433/29; 600/172, 600/173; 396/322, 323, 333

(56) References Cited

U.S. PATENT DOCUMENTS

| | | | |
|---|---|---|---|
| 4,082,953 A | 4/1978 | Krause et al. .............. 250/413 |
| 4,160,997 A | 7/1979 | Schwartz ..................... 358/93 |
| 4,494,950 A | 1/1985 | Fischell ....................... 604/66 |
| 4,575,805 A | 3/1986 | Moermann et al. .......... 364/474 |
| 4,611,347 A | 9/1986 | Netravali et al. ............. 382/27 |
| 4,629,424 A | 12/1986 | Lauks et al. .................... 433/6 |
| 4,633,304 A | 12/1986 | Nagasaki ..................... 358/98 |
| 4,658,669 A | 4/1987 | Nishikawa ................... 74/531 |
| 4,797,101 A | 1/1989 | Morris ........................ 433/229 |
| 4,835,410 A | 5/1989 | Bhagwat et al. .............. 307/64 |
| 4,858,001 A | 8/1989 | Milbank et al. .............. 358/98 |
| 4,981,141 A | 1/1991 | Segalowitz ................. 128/696 |
| 4,987,897 A | 1/1991 | Funke ....................... 128/419 |
| 5,113,859 A | 5/1992 | Funke ....................... 128/419 |
| 5,115,307 A | 5/1992 | Cooper et al. ................ 358/98 |
| 4,858,001 A | 6/1992 | Milbank et al. .............. 358/98 |
| 5,212,476 A | 5/1993 | Maloney ................ 340/825.19 |
| 5,257,184 A | 10/1993 | Mushabac .............. 364/413.28 |
| 5,264,935 A | 11/1993 | Nakajima ..................... 358/181 |
| 5,361,108 A | * 11/1994 | Kamata et al. ............. 396/333 |
| 5,373,852 A | 12/1994 | Harrison et al. ............ 128/733 |
| 5,381,264 A | 1/1995 | Wickholm et al. .......... 359/419 |
| 5,434,418 A | 7/1995 | Schick ................... 250/370.11 |
| 5,454,022 A | 9/1995 | Lee et al. .................. 378/98.8 |
| 5,471,518 A | 11/1995 | Barber et al. ................. 379/58 |
| 5,514,873 A | 5/1996 | Schulze-Ganzlin et al. . 250/394 |
| 5,523,782 A | 6/1996 | Williams ...................... 348/66 |
| 5,527,261 A | 6/1996 | Monroe et al. ............. 600/109 |
| 5,551,953 A | 9/1996 | Lattin et al. .................. 604/20 |
| 5,568,192 A | 10/1996 | Hannah ...................... 348/227 |
| 5,610,657 A | 3/1997 | Zhang ........................ 348/415 |
| 5,702,249 A | 12/1997 | Cooper ........................ 433/29 |
| 5,712,482 A | 1/1998 | Gaiser et al. .......... 250/363.08 |
| 5,712,682 A | 1/1998 | Hannah ...................... 348/255 |
| 5,737,013 A | 4/1998 | Williams et al. .............. 348/66 |

(Continued)

FOREIGN PATENT DOCUMENTS

| | | | | |
|---|---|---|---|---|
| DE | 4009438 A1 | 9/1991 | .......... H04N/5/247 |
| EP | 0583908 A | 2/1994 | |
| JP | 100179516 A | * 7/1998 | |
| WO | WO 9603917 A | 2/1996 | ............ A61B/6/14 |
| WO | WO 98/10587 A | 3/1998 | |
| WO | WO 98/15227 A | 4/1998 | ............ A61B/6/14 |
| WO | WO 98/20796 A | 5/1998 | ............ A61B/6/14 |
| WO | WO 99/60786 A1 | 11/1999 | ............ H04N/5/76 |

Primary Examiner—Ralph A. Lewis
(74) Attorney, Agent, or Firm—Fitzpatrick, Cella, Harper & Scinto

(57) ABSTRACT

A dental camera is provided having multiple lenses. The dental camera has at least a first lens for use in an intra-oral mode, and at least a second lens for use in an extra-oral mode. The dental camera is switchable between the intra-oral mode and the extra-oral mode. Each lens is associated with an image sensor, for example, a CMOS active pixel sensor or a charge-coupled device.

36 Claims, 3 Drawing Sheets

U.S. PATENT DOCUMENTS

| | | | |
|---|---|---|---|
| 5,742,407 A | 4/1998 | Albrecht et al. | 358/496 |
| 5,745,165 A | 4/1998 | Atsuta et al. | 348/65 |
| 5,771,067 A | 6/1998 | Williams et al. | 348/66 |
| 5,773,832 A | 6/1998 | Sayed et al. | 250/370.09 |
| 5,777,254 A | 7/1998 | Fay et al. | 84/613 |
| 5,778,218 A | 7/1998 | Guilick | 395/558 |
| 5,873,814 A | 2/1999 | Adair | 600/109 |
| 5,879,289 A | 3/1999 | Yarush et al. | 600/179 |
| 5,880,826 A | 3/1999 | Jung et al. | 356/73 |
| 5,908,294 A | 6/1999 | Schick et al. | 433/29 |
| 5,912,942 A | 6/1999 | Schick et al. | 378/98.8 |
| 5,919,129 A | 7/1999 | Vandre | 600/170 |
| 5,940,126 A * | 8/1999 | Kimura | 348/294 |
| 5,969,750 A | 10/1999 | Hsieh et al. | 348/15 |
| 5,976,076 A * | 11/1999 | Kolff et al. | 600/166 |
| 6,002,424 A | 12/1999 | Rapa et al. | 348/66 |
| 6,093,019 A | 7/2000 | Morandi et al. | 433/29 |
| 6,106,457 A | 8/2000 | Perkins et al. | 600/175 |
| 6,132,211 A | 10/2000 | Peithman | 433/29 |
| 6,134,298 A | 10/2000 | Schick et al. | 378/98.8 |
| 6,149,300 A | 11/2000 | Greenway et al. | 378/191 |
| 6,186,944 B1 | 2/2001 | Tsai | 600/200 |
| 6,201,880 B1 | 3/2001 | Elbaum et al. | 382/100 |
| 6,210,159 B1 | 4/2001 | Lehmann et al. | 433/26 |
| 6,328,567 B1 | 12/2001 | Morris et al. | 433/215 |
| 6,561,972 B2 * | 5/2003 | Ooshima et al. | 600/173 |
| 6,608,668 B2 * | 8/2003 | Gharib et al. | 356/28 |
| 6,674,462 B1 * | 1/2004 | Ooshima et al. | 348/42 |
| 6,717,752 B2 * | 4/2004 | Kanai | 359/814 |
| 2001/0052930 A1 | 12/2001 | Adair et al. | 348/65 |

* cited by examiner

DENTAL CAMERA UTILIZING MULTIPLE LENSES

BACKGROUND OF THE INVENTION

1. Field of the Invention

This invention relates generally to the field of dental cameras, and more particularly to a dental camera system having at least two lenses selectable for either intra-oral or extra-oral use.

2. Related Art

For many years, clinicians in the dental industry used dental mirrors to more clearly visualize and diagnose hidden areas in a patient's mouth. These mirrors remain useful in certain respects, but significant limitations exist. First, it is often difficult to visualize a dental structure using dental mirrors, because the image must be reflected into the viewer's line of sight. Second, mirrors provide a relatively small image that can be difficult to see. Third, providing the lighting necessary to illuminate fully the area being reflected by the mirror remains a challenge. Furthermore, when using mirrors it is often difficult to communicate information to the patient or to other clinicians, because the image to be visualized is dependent upon the viewer's position relative to the mirror.

In order to address these and other significant limitations associated with using mirrors to visualize and diagnose areas in a patient's mouth, dental cameras were introduced into the field, and are now widely used within the dental industry to enhance the practitioner's ability to view the patient's dental anatomy. Dental cameras are also useful in providing the patient with a visual understanding of his or her clinical options.

Dental cameras provide advantages over dental mirrors in several respects. First, they do not require positioning towards a reflected angle. Second, they typically have built-in light sources which illuminate the area being visualized. Third, dental cameras are useful in obtaining a permanent record of the condition of a patient's mouth. Furthermore, they can be used as "teaching tools" to communicate information to others since the images appear on a monitor, and therefore more people than simply the dental practitioner may view their output.

Dental cameras typically comprise an internal base station that provides power, light and video processing to a handpiece, which contains an image sensor and optics. The light is typically provided via a flexible fiber optic bundle. Most dental cameras have one lens with a focusing mechanism that allows the dentist to view the near field for intra-oral use and the far field for extra-oral use.

The first cameras were merely adaptations of video endoscopes used in the field of medicine. U.S. Pat. No. 4,858,001 to Milbank et al. provides an example of an early dental camera. Milbank et al. discusses a hand-held endoscopic apparatus consisting of a body, a camera and a removable and interchangeable image-gathering element capable of presenting an image of an object to the camera. The image-gathering element, also called an objective element, may enable viewing of an image at varying angles because it may be flexible or rigid and may be of a variety of sizes and shapes. The objective element connects to a handpiece which has a hollow or tubular body portion rotatably carrying a central shaft upon which is mounted a video camera arrangement, such as, for example, a CCD mosaic chip camera. The tubular design is suited for penetration into the convoluted cavity of the human body.

Dental cameras, however, have particular requirements not addressed by most endoscopes. One challenge is to develop a camera suitable for both intra-oral and extra-oral imaging, each of which carries certain requirements which differ from the requirements carried by the other. For example, an intra-oral camera requires an illumination source and a wider angle as compared with an extra-oral camera.

U.S. Pat. No. 5,702,249 to Cooper made some early contributions to the field of dental cameras, taking these issues into account and creating a device more suitable to the applications for which it is used. Cooper discusses a modular intra-oral camera with a removable objective element that enables various lenses to be used interchangeably. Unfortunately, while the Cooper structure offers some flexibility, it also requires magnification changing means, aperture changing means, and light dispersion changing means to be coupled with the focusing means, thereby adding an unnecessary layer of complexity into the design of the camera. Furthermore, swapping the various objective lenses is clearly cumbersome for the dentist, and introduces a potential failure mechanism.

U.S. Pat. No. 5,771,067 to Williams et al. proposes an alternative design to Cooper. Williams et al. provides a dental camera including an adjustably focusing lens, and an electrically adjustable iris which may be progressively closed and opened to focus between the near field and the far field. More particularly, the iris is adjustable between a nearly closed opening and a wide opening in response to the focusing adjustment between the near field of focus and the far field of focus. Unfortunately, this strategy still requires the dentist to adjust a knob, which is a cumbersome task, particularly when the dentist is in the middle of a procedure.

Williams et al. also shares a disadvantage with Cooper, in that the location of the lens on the handpiece is fixed. More specifically, the location of the lens in these devices is on the distal tip, a location that is convenient for intra-oral use, but physically awkward for extra-oral use. In addition, imaging parameters such as white balance cannot be easily optimized for specific applications. Finally, in power constrained designs such as wireless cameras, the lamps that are required to provide illumination in intra-oral applications, but are not required for extra-oral applications, would often draw unnecessary power.

U.S. Pat. No. 5,381,264 to Wickholm et al. proposes another approach, namely a multiple field of view sensor lens assembly. The Wickholm et al. device includes a rotatable telescope for providing first and second fields of view for the sensor. In Wickholm et al., a rotatable lens assembly enables two objective elements with different fields of view to be placed at orthogonal planes to one another. Wickholm et al., however, suffers from many of the same disadvantages as the Williams et al. patent. Moreover, Wickholm et al. is not specific to, and not particularly suited for, the field of dentistry.

As explained above, providing a dental camera with the capability of effectively viewing the near field for intra-oral use and the far field for extra-oral use presents unique challenges due to certain inherent problems. Namely, the two environments have significantly different imaging requirements that cannot be easily accommodated by one lens system. First, the distance from the lens to the object is typically short intra-orally, but further extra-orally. Second, as mentioned above, the camera requires illumination intra-orally but not extra-orally. Third, the white balance compensation is different when the camera provides its own illumination (i.e., when the camera is used intra-orally) than when the illumination is from ambient light (i.e., when the camera is used extra-orally). Fourth, the optimal location of the lens on the handpiece differs for the extra-oral camera application as opposed to the intra-oral camera application.

Further challenges and differences relate to the aperture of the camera. The aperture is an opening in a lens that light passes through. Adjusting the size of the aperture controls the exposure level of the light. The wider the lens aperture, the more rays of light (photons) the lens can collect. A smaller aperture makes focusing less critical, and gives a lens a greater depth of field because it cuts off the more divergent beams of photons that would have to be focused. For intra-oral use a small aperture is desirable, in order to maximize the depth of field; whereas for extra-oral use a large aperture is typically desirable, in order to maximize brightness by letting more light into the camera.

It has previously been impractical to house these systems (with either one or multiple lenses) entirely within the handpiece, as the resulting camera would be too large and bulky. Most dental camera systems therefore suffer from limited portability.

There exists, therefore, a great need for a dental camera which takes an entirely fresh approach, and overcomes the above-mentioned obstacles which have heretofore plagued the prior art.

SUMMARY OF THE INVENTION

This invention teaches a dental camera having at least two lenses, one an intra-oral lense and one an extra-oral lens. The intra-oral lens preferably contains white LEDs to illuminate the inside of the mouth. The handpiece has a button located thereon for switching the mode of operation between the two lenses to effect intra-oral imaging and extra-oral imaging.

Providing a dental camera with multiple fixed focus lenses offers many advantages. First, it is not necessary for the dental practitioner to adjust the focus; rather, the camera is merely selectable for either intra-oral or extra-oral use. Second, the camera has no moving parts. Third, each lens can be optimized to suit a specific application; for example, the extra-oral lens does not require illumination, so none may be provided for that mode, thereby saving power. Furthermore, each lens can be placed in a preferred and optimal location on the handpiece, which allows for easier operation.

Since numerous applications for dental cameras require acquisition of both intra-oral and extra-oral images, it is an object of this invention to provide a system having at least two lenses to accommodate both applications. As mentioned above, each lens may be placed in an optimal location on the handpiece and may be customized to account for the various focus, lighting, and white balance compensation requirements depending upon the lens function.

In a preferred embodiment, a CMOS active pixel sensor (APS) chip having an analog output is utilized, which offers several advantages. Circuitry, such as an analog-to-digital converter and video compression circuitry, may be incorporated into the image sensor, which eliminates the need for a separate computer board, thereby reducing occupied space. This becomes further advantageous because an RF transmitter, for example, may be incorporated into this freed space to provide a wireless camera. And, due to the lower power requirements of active pixel sensors (APS), a rechargeable battery may be implemented as well.

The invention in one embodiment provides a dental camera having multiple lenses, comprising at least a first lens for use in an intra-oral mode, and at least a second lens for use in an extra-oral mode, wherein the dental camera is switchable between the intra-oral mode and the extra-oral mode.

The first lens may be a fixed-focus lens and the second lens may be a variable-focus lens. Or the first and second lenses may be fixed-focus lenses. Alternatively, the first lens may be a variable-focus lens and the second lens may be a fixed-focus lens. Further, the first and second lenses may be variable-focus lenses. Each lens may be associated with a CMOS active pixel sensor. Alternatively, each lens may be associated with a charge-coupled device.

The invention in another embodiment provides a dental camera comprising at least two lenses, the dental camera being operable in an intra-oral mode which utilizes a first lens, and an extra-oral mode which utilizes a second lens, wherein the dental camera is switchable between the two modes, and wherein a light source is activated during the intra-oral mode. The light source may comprise a plurality of white LEDs.

The invention in another embodiment provides a dental camera having multiple lenses, comprising a first image sensor associated with a first lens customized for use in an intra-oral mode, and a second image sensor associated with a second lens customized for use in an extra-oral mode, the first lens placed distal to the second lens, wherein the dental camera is switchable between the intra-oral mode and the extra-oral mode. The dental camera may further comprise a light source for use in the intra-oral mode. The light source may be a plurality of white LEDs.

The invention in another embodiment provides a wireless dental camera system having multiple lenses, comprising: a first image sensor associated with a first lens for use in an intra-oral mode; a second image sensor associated with a second lens for use in an extra-oral mode; a light source for use in the intra-oral mode; a control circuit for processing digital signals representing video images from the image sensors, for controlling switching between the intra-oral mode and the extra-oral mode, and for controlling power supplied to the lenses; a power module for supplying power to the control circuit; a transmitter for transmitting the digital signals; a receiver for receiving the digital signals; and a base station for supplying the received digital signals to an image processing unit. The power module may comprise a rechargeable battery. The base station may supply the received digital signals to the image processing system via a Universal Serial Bus.

The invention in another embodiment comprises a dental camera system having multiple lenses, comprising: a first image sensor associated with a first lens for use in an intra-oral mode; a second image sensor associated with a second lens for use in an extra-oral mode; a light source for use in the intra-oral mode; a control circuit for processing digital signals representing video images from the image sensors, for controlling switching between the intra-oral mode and the extra-oral mode, and for controlling power supplied to the lenses; and a cable for providing the digital signals to a digital port on an image processing unit, and for providing power from the image processing unit to the dental camera system.

The invention in another embodiment provides a dental camera comprising at least two lenses selectable for either intra-oral use or extra-oral use.

The invention in another embodiment provides a dental camera, comprising means for acquiring intra-oral images in an intra-oral mode, and means for acquiring extra-oral images in an extra-oral mode, wherein the dental camera is switchable between the intra-oral mode and the extra-oral mode.

The invention will next be described in connection with certain exemplary embodiments; however, it should be clear to those skilled in the art that various modifications, additions, and subtractions can be made without departing from the spirit or scope of the claims.

DETAILED DESCRIPTION OF THE INVENTION

Figure 1:
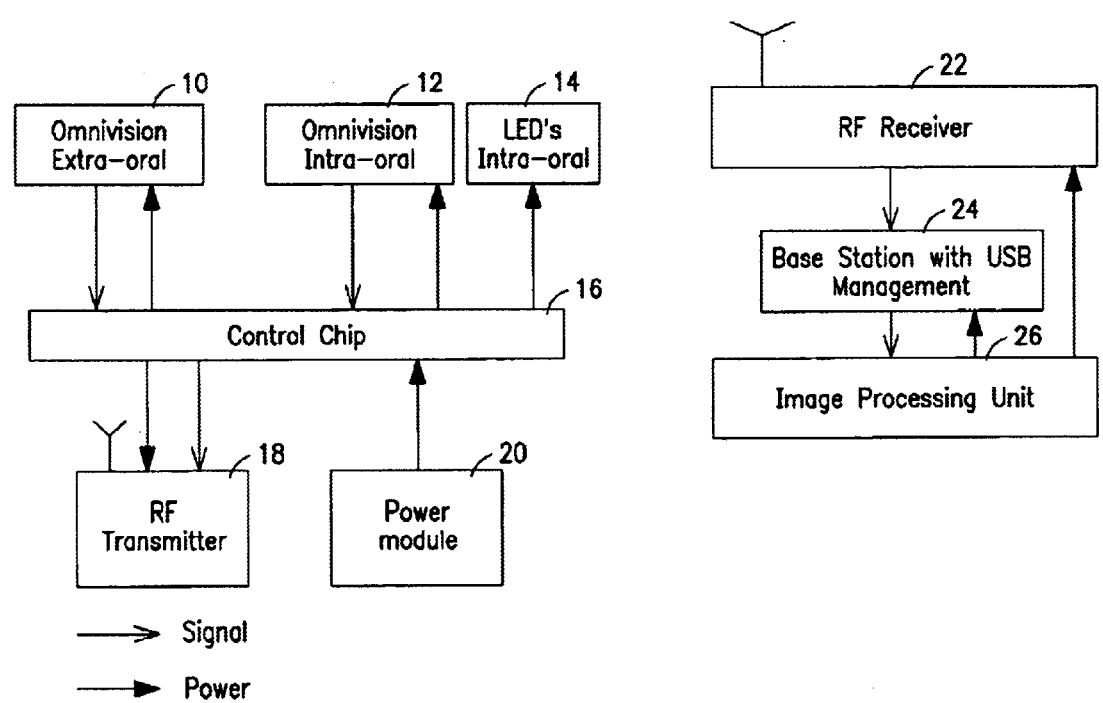
FIG. 1 illustrates a block diagram of a wireless dental camera system according to one embodiment.

As explained above, the present invention relates to a dental camera having at least two lenses, selectable for switching between an intra-oral mode and an extra-oral mode. Each lens may be either a fixed focus or a variable-focus lens. A fixed-focus lens is a lens whereby the distance from the lens to the sensor is physically fixed. As a result, a fixed-focus lens creates a sharp image at only one distance to its subject. A variable-focus lens is a zoom lens, i.e., one in which focal length is variable. Elements inside a variable-focus lens shift their positions, enabling the lens to change its focal length, in effect providing one lens that has many focal lengths.

In order to implement the multiple lenses, in one embodiment of the present invention, the dental camera comprises two or more image sensors which generate image signals. The image sensors may be CMOS active pixel sensors (APS), such as for example an Omnivision OV7910N CMOS APS array. In accordance with the present invention, each sensor has an associated lens. One significant advantage of CMOS detectors is that they are able to be manufactured with auxiliary circuitry. Thus, as explained above, circuitry such as an analog-to-digital (A/D) converter may be incorporated within the imaging sensor, thereby eliminating the need for separate computer boards and reducing occupied space. Alternatively, other imaging chips, such as charge-coupled devices (CCDs) may be utilized. Such other imaging chips would require other components such as an A/D converter and driver circuitry to be included either in the camera handpiece or in the remote base station.

As explained above, the dental camera is switchable between an intra-oral mode and an extra-oral mode. The intra-oral lens and chip may be housed on the distal end of the handpiece. For intra-oral imaging, the interior of the mouth must be illuminated. Therefore, in a preferred embodiment, the intra-oral lens system contains white light emitting diodes (LEDs), such as the type as described in U.S. Pat. No. 5,908,294 to Schick et al., the entirety of which is hereby incorporated by reference. The white LED could comprise, for example, a short-wavelength LED combined together with a phosphorescent coating, such as Nichia America # NSCW-100. The white LED could also comprise, for example, a set of three single color LEDs (e.g., red, green, and blue), mounted in a single package, such as Nichia America # NSCM-310. Light sources other than white LEDs may also be used, such as, for example, a wide variety of lamps, e.g., a halogen lamp coupled to the system via a flexible fiber-optic cable. A low-power, long-life lamp may be preferable to save power and minimize service calls and system down time. One example of a suitable lamp is an incandescent light bulb, such as Gilway Technical Lamp # 4115.

The extra-oral lens may be located proximally on the camera, as opposed to the distal location of the intra-oral lens, and typically does not require a light source. In accordance with the present invention, the placement of the two lenses may be optimized for their intended use. In alternative embodiments, other lenses and computer chips may also be incorporated for their specialized applications.

Various embodiments of the invention may be readily envisioned. For example, the camera may be wireless or wired. Transmission may be analog or digital. In one embodiment, the overall schematics of the invention may consist of two top-level components, namely, a camera and a base station. In another embodiment, the base station may not be necessary if the camera is wired to a port capable of both providing power and handling data transfer, such as is described in U.S. patent application Ser. No. 10/225,350, the entirety of which is hereby incorporated by reference. Ports capable of such include the USB (Universal Serial Bus) or the PCMCIA port (Personal Computer Memory Card International Association).

FIG. 1 illustrates a schematic of a wireless embodiment. A wireless mode is advantageous because the dentist is not constrained by cords emanating from the camera. In FIG. 1, an APS extra-oral chip 10, an APS intra-oral chip 12, and a single LED light source 14 used for intra-oral imaging are linked to a control chip 16 that may control sensor power and data transfer. The control chip 16 may also control certain buttons on the handpiece which carry out certain functions. For example, a button may be located on the proximal end of the handpiece and may be used to switch the mode of operation between the intra-oral mode and the extra-oral mode. Another button may be incorporated to freeze image acquisition. Other buttons having various functionality may be readily envisioned by those skilled in the art.

Further, in the wireless mode, the camera requires a power module 20. The power module preferably includes a replaceable battery with sufficient service life or a rechargeable battery which when fully charged can provide enough power for several clinical examinations. If a rechargeable battery is used, the handpiece chassis contains recessed pins that are used to recharge the system. When not in use, the camera rests in a cradle that recharges the battery and toggles the camera on and off. Utilizing a low power chip such as CMOS APS and a low power light source such as LEDs allows for a longer service life. Suitable types of batteries for powering the camera include, but are not limited to, nickel-cadmium, nickel-metal-hydride, lithium manganese dioxide, and lithium ion. In any event, the battery must provide a significant amount of power to meet the needs of the circuitry and must be small enough to fit within the slim profile that is preferred clinically. This can be technically difficult given the large power requirements of solid state sensors and radio-frequency transmitters.

The RF transmitter 18 receives image data signals from an image sensor. Alternatively, a wired link such as a direct USB (Universal Serial Bus) connection may be utilized. The absence of additional A/D and driver circuitry enables the RF components to be included in the camera's slim profile. A high reliability RF link is essential since the pulses must be transmitted from within a camera inside a patient's mouth. Because the data transfer should be continuous, a high-speed link is required. As understood by those, skilled in the art, the carrier is modulated with the digital signal provided by the Omnivision chip (for example) through the microcontroller using frequency shift keying and transmitted at a frequency compliant with European and United States regulatory requirements. The effective transmission range is preferably at least 10 feet, thereby allowing the clinician freedom in where he or she chooses to place the receiver. The camera transmits periodic carrier bursts to allow the host computer to gauge the RF link status and ensure that it is ready for use.

Regarding the base station 24 which communicates with the image processing unit 26, the RF receiver 22 demodulates the modulated carrier to restore the original base band signal. Control logic may be implemented to facilitate operations such as the Manchester conversion, digital filtering, and the suppression of unwanted signals. If transmission is analog, analog-to-digital conversion (ADC) would also be accomplished at the base station. These steps are necessary to assure reliable communication between the base station and camera. The data may be exported from the base station 24 using one or more of a multitude of commonly used ports including but not limited to the USB. In the preferred embodiment, the USB not only provides data output capability, but also supplies power to the base station. Power supply could of course be achieved through alternative means as would be known to those skilled in the art. In this embodiment, USB management is also carried out by the base station.

The USB is a serial 12 megabit per second (Mbps) channel that can be used for peripherals. The USB is a token-based bus; that is, the USB host controller broadcasts tokens on the bus and a device that detects a match on the address in the token responds by either accepting or sending data to the host. The host also manages USB bus power by supporting suspend/resume operations. The USB is advantageous in that it does not require the use of specially designed hardware inside the computer; once the appropriate software has been installed, a peripheral can be plugged into the USB port.

Figure 2:
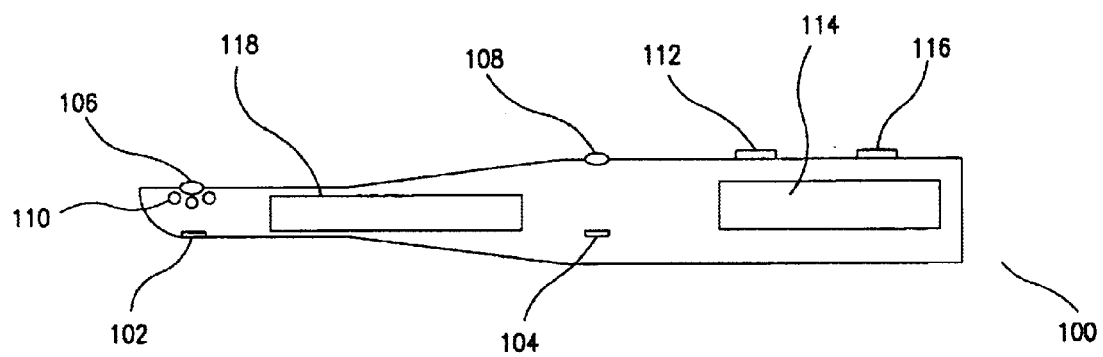
FIG. 2 illustrates a wireless dental video camera and shows the placement of each lens on the handpiece according to a preferred embodiment.

FIG. 2 illustrates a wireless dental video camera 100 and shows the placement of each lens on the handpiece according to a preferred embodiment. The camera 100 has two image sensors 102, 104, which may be, for example, CMOS active pixel sensor (APS) chips. Each image sensor 102 and 104 has an associated lens; image sensor 102 is associated with intra-oral lens 106, while image sensor 104 is associated with extra-oral lens 108. In the embodiment illustrated in FIG. 2, intra-oral lens 106 is placed at the distal end of the handpiece, enabling the dental practitioner to easily visualize and film the inside of a patient's mouth. A plurality of white LEDs 110 are provided near the intra-oral lens 106, in order to provide illumination intra-orally. The dental camera 100 includes a power module 118, which may be, for example, a battery, for providing ample power for several clinical examinations.

The wireless camera illustrated in FIG. 2 also includes a intra-oral/extra-oral button 112 located at a proximal end of the handpiece for switching between intra-oral mode and extra-oral mode. Reference numeral 114 denotes a transmitter/control chip. The control chip controls functionality of the camera, such as sensor power and data transfer, and carries out those functions enabled by the buttons on the handpiece, such as the intra-oral/extra-oral button 112 and on/off button 116. Other buttons are not shown in FIG. 2, but may be added to implement other functions, such as those relating to image acquisition. The transmitter effects wireless transmission of the data to a receiver, base station, and image processing unit (not shown in FIG. 2) for viewing the images.

Figure 3:
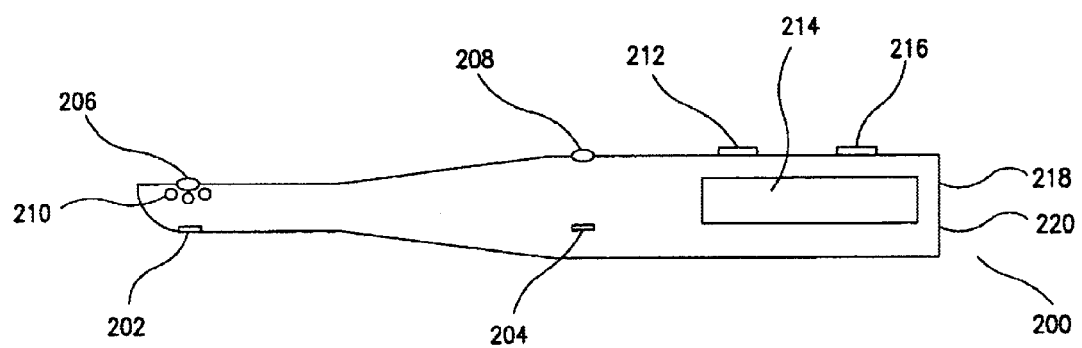
FIG. 3 illustrates a dental camera in a wired embodiment, according to the invention.

FIG. 3 illustrates a dental camera 200 in a wired embodiment, according to the invention. The camera 200 has two image sensors 202, 204, which may be, for example, CMOS active pixel sensor (APS) chips. Each image sensor 202 and 204 has an associated lens; image sensor 202 is associated with intra-oral lens 206, and image sensor 204 is associated with extra-oral lens 208. Intra-oral lens 206 is placed at the distal end of the handpiece, thereby enabling the dental practitioner to easily visualize and film the inside of a patient's mouth. A plurality of white LEDs 210 are provided near the intra-oral lens 206, in order to provide illumination when the camera is in intra-oral mode.

Intra-oral/extra-oral button 212 located at a proximal end of the handpiece is used for switching between intra-oral mode and extra-oral mode. Control chip 214 controls functionality of the camera, such as sensor power and data transfer, and carries out those functions enabled by the buttons on the handpiece, such as the intra oral/extra-oral button 212 and on/off button 216. Other buttons may be added to the camera to implement various other functions. Cables 218 and 220 provide power and transfer the data to an image processing unit (not shown) via USB or NTSC (National Television Systems Committee) for viewing the images.

While the invention has been particularly shown and described with respect to preferred embodiments thereof, it will be understood by those skilled in the art that changes in form and details may be made therein without departing from the scope and spirit of the invention.

Having described the invention, what is claimed as new and secured by Letters Patent is:

1. A dental camera having multiple lenses, comprising:
a first image sensor for use in an intra-oral mode;
at least a first lens in an optical path of the first image sensor for use in the intra-oral mode;
a second image sensor for use in an extra-oral mode;
at least a second lens in an optical path of the second image sensor for use in the extra oral mode; and
a controller that selectively enables one of the first image sensor and the second image sensor to switch the dental camera between the intra-oral mode and the extra-oral mode.

2. A dental camera as set forth in claim 1, wherein the first lens is a fixed-focus lens and the second lens is a variable-focus lens.

3. A dental camera as set forth in claim 1, wherein the first and second lenses are fixed-focus lenses.

4. A dental camera as set forth in claim 1, wherein the first lens is a variable-focus lens and the second lens is a fixed-focus lens.

5. A dental camera as set forth in claim 1, wherein the first and second lenses are variable-focus lenses.

6. The dental camera as set forth in claim 1, wherein each lens is associated with a CMOS active pixel sensor.

7. The dental camera as set forth in claim 1, wherein each lens is associated with a charge-coupled device.

8. A dental camera comprising at least two lenses, said dental camera being operable in:
an intra-oral mode which utilizes a first image sensor and a first lens in an optical path of the first image sensor; and an extra-oral mode which utilizes a second image sensor and a second lens in an optical path of the second image sensor, wherein the dental camera is switchable between the two modes by selectively enabling one of the first image sensor and the second image sensor, and wherein a light source is activated during the intra-oral mode.

9. A dental camera as set forth in claim 8, wherein the first lens is a fixed-focus lens and the second lens is a variable-focus lens.

10. A dental camera as set forth in claim 8, wherein the first and second lenses are fixed-focus lenses.

11. A dental camera as set forth in claim 8, wherein the first lens is a variable-focus lens and the second lens is a fixed-focus lens.

12. A dental camera as set forth in claim 8, wherein the first and second lenses are variable-focus lenses.

13. A dental camera as set forth in claim 8, wherein the light source comprises a plurality of white LEDs.

14. The dental camera as set forth in claim 8, wherein each lens is associated with a CMOS active pixel sensor.

15. The dental camera as set forth in claim 8, wherein each lens is associated with a charge-coupled device.

16. A dental camera having multiple lenses, comprising:
a first image sensor having a first lens in its optical path and customized for use in an intra-oral mode, and
a second image sensor having a second lens in its optical path and customized for use in an extra-oral mode, the first lens placed distal to the second lens,
wherein the dental camera is switchable between the intra-oral mode and the extra-oral mode by selectively enabling one of the first image sensor and the second image sensor.

17. A dental camera as set forth in claim 16, wherein the first lens is a fixed-focus lens and the second lens is a variable-focus lens.

18. A dental camera as set forth in claim 16, wherein the first and second lenses are fixed-focus lenses.

19. A dental camera as set forth in claim 16, wherein the first lens is a variable-focus lens and the second lens is a fixed-focus lens.

20. A dental camera as set forth in claim 16, wherein the first and second lenses are variable-focus lenses.

21. The dental camera as set forth in claim 16, further comprising a light source for use in the intra-oral mode.

22. The dental camera as set forth in claim 16, wherein the light source is a plurality of white LEDs.

23. The dental camera as set forth in claim 16, wherein the first and second image sensors are CMOS active pixel sensors.

24. The dental camera as set forth in claim 16, wherein the first and second image sensors are charge-coupled devices.

25. A wireless dental camera system having multiple lenses, comprising:
a first image sensor having a first lens in its optical path and adapted for use in an intra-oral mode;
a second image sensor having a second lens in its optical path and adapted for use in an extra-oral mode;
a light source for use in the intra-oral mode;
a control circuit for processing digital signals representing video images from the image sensors, for controlling switching between the intra-oral mode and the extra-oral mode by selectively enabling one of the first image sensor and the second image sensor, and for controlling power supplied to the lenses;
a power module for supplying power to the control circuit;
a transmitter for transmitting the digital signals;
a receiver for receiving the digital signals; and
a base station for supplying the received digital signals to an image processing unit.

26. A dental camera system as set forth in claim 25, wherein the first lens is a fixed-focus lens and the second lens is a variable-focus lens.

27. A dental camera system as set forth in claim 25, wherein the first lens is a fixed-focus lens and the second lens is a fixed-focus lens.

28. A dental camera system as set forth in claim 25, wherein the first lens is a variable-focus lens and the second lens is a fixed-focus lens.

29. A dental camera system as set forth in claim 25, wherein the first lens is a variable-focus lens and the second lens is a variable-focus lens.

30. The dental camera system as set forth in claim 25, wherein the power module comprises a rechargeable battery.

31. The dental camera system as set forth in claim 25, wherein the light source comprises a plurality of white LEDs.

32. A dental camera system as set forth in claim 25, wherein the base station supplies the received digital signals to the image processing system via a Universal Serial Bus.

33. The dental camera as set forth in claim 25, wherein the first and second image sensors are CMOS active pixel sensors.

34. The dental camera as set forth in claim 25, wherein the first and second image sensors are charge-coupled devices.

35. A dental camera system having multiple lenses, comprising:
a first image sensor having a first lens in its optical path and adapted for use in an intra-oral mode;
a second image sensor having a second lens in its optical path and adapted for use in an extra-oral mode;
a light source for use in the intra-oral mode;
a control circuit for processing digital signals representing video images from the image sensors, for controlling switching between the intra-oral mode and the extra-oral mode by selectively enabling one of the first image sensor and the second image sensor, and for controlling power supplied to the lenses; and
a cable for providing the digital signals to a digital port on an image processing unit, and for providing power from the image processing unit to the dental camera system.

36. A dental camera, comprising:
means for acquiring intra-oral images in an intra-oral mode, including first image sensing means and first lens means in an optical path of the first image sensing means; and
means for acquiring extra-oral images in an extra-oral mode, including second image sensing means and second lens means in an optical path of the second image sensing means,
wherein the dental camera is switchable between the intra-oral mode and the extra-oral mode by selectively enabling one of the first image sensing means and the second image sensing means.

* * * * *